United States Patent
Couture (10) Patent No.: US 9,717,548 B2
(45) Date of Patent: Aug. 1, 2017

(54) ELECTRODE FOR USE IN A BIPOLAR ELECTROSURGICAL INSTRUMENT

(71) Applicant: COVIDIEN LP, Mansfield, MA (US)

(72) Inventor: Gary M. Couture, Longmont, CO (US)

(73) Assignee: Covidien LP, Mansfield, MA (US)

( * ) Notice: Subject to any disclaimer, the term of this patent is extended or adjusted under 35 U.S.C. 154(b) by 266 days.

(21) Appl. No.: 14/295,049

(22) Filed: Jun. 3, 2014

(65) Prior Publication Data
US 2015/0088128 A1 Mar. 26, 2015

Related U.S. Application Data

(60) Provisional application No. 61/881,529, filed on Sep. 24, 2013.

(51) Int. Cl.
*A61B 18/18* (2006.01)
*A61B 18/14* (2006.01)
*A61B 18/00* (2006.01)

(52) U.S. Cl.
CPC ...... *A61B 18/1445* (2013.01); *A61B 2018/00589* (2013.01); *A61B 2018/00601* (2013.01);
(Continued)

(58) Field of Classification Search
CPC ...... A61B 18/1445; A61B 2018/00589; A61B 2018/00601; A61B 2018/00607; A61B 2018/1452
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

U.S. Appl. No. 13/731,674, filed Dec. 31, 2012; inventor: Siebrecht.
(Continued)

*Primary Examiner* — Michael Peffley
*Assistant Examiner* — Amanda Zink (57) ABSTRACT

A end-effector assembly includes opposing first and second jaw assemblies, at least one of the first and second assemblies movable relative to the other from a first position wherein the jaw assemblies are disposed in spaced relation relative to one another to at least a second position closer to one another wherein the jaw assemblies cooperate to grasp tissue therebetween. The first jaw assembly includes a first housing and a first electrically-conductive tissue-engaging structure associated with at least a portion of the first housing. The second jaw assembly includes a second housing and a second electrically-conductive tissue-engaging structure associated with at least a portion of the second housing. The end-effector assembly includes a dissector electrode coupled along at least a portion of a lateral side portion of either one of the first housing or the second housing. The dissector electrode is electrically-isolated from the first and second electrically-conductive tissue-engaging structures.

18 Claims, 5 Drawing Sheets

(52) U.S. Cl.
CPC ............. *A61B 2018/00607* (2013.01); *A61B 2018/1452* (2013.01)

(58) Field of Classification Search
USPC .................................................... 606/45–52
See application file for complete search history.

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,658,281 A | 8/1997 | Heard | |
| D384,413 S | 9/1997 | Zlock et al. | |
| 5,755,717 A * | 5/1998 | Yates | A61B 18/1482 606/41 |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| 7,147,637 B2 * | 12/2006 | Goble | A61B 18/1442 606/50 |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,419,490 B2 | 9/2008 | Falkenstein et al. | |
| D582,038 S | 12/2008 | Swoyer et al. | |
| 7,549,990 B2 | 6/2009 | Canady | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| 8,262,655 B2 | 9/2012 | Ghabrial et al. | |
| D670,808 S | 11/2012 | Moua et al. | |
| D680,220 S | 4/2013 | Rachlin | |
| 2004/0006340 A1 * | 1/2004 | Latterell | A61B 18/1442 606/48 |
| 2006/0064086 A1 | 3/2006 | Odom | |
| 2009/0248007 A1 * | 10/2009 | Falkenstein | A61B 18/1445 606/33 |
| 2010/0036370 A1 | 2/2010 | Mirel et al. | |
| 2011/0282339 A1 * | 11/2011 | Weizman | A61B 18/1445 606/33 |
| 2012/0059371 A1 * | 3/2012 | Anderson | A61B 18/1445 606/45 |
| 2012/0059374 A1 | 3/2012 | Johnson et al. | |
| 2012/0253344 A1 * | 10/2012 | Dumbauld | A61B 18/1445 606/52 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1767163 A1 | 3/2007 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |

(56) References Cited

FOREIGN PATENT DOCUMENTS

| | | |
|---|---|---|
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2007118608 A1 | 10/2007 |
| WO | 2008/040483 A1 | 4/2008 |
| WO | 2011/018154 A1 | 2/2011 |

OTHER PUBLICATIONS

U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight And Absorbance Imaging Of Biologic Media", Science, American Association for the Advancement of Science, Washington, DC, vol. 259, Mar. 5, 1993, pp. 1463-1466.

(56) References Cited

OTHER PUBLICATIONS

Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing For Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.
International Search Report and Written Opinion of the International Searching Authority, issued Dec. 1, 2014, corresponding to International Application No. PCT/US2014/052212; 10 total pages.
European Search Report dated Jun. 6, 2017, corresponding to European Application No. 14848376.1; 5 pages.

\* cited by examiner

ELECTRODE FOR USE IN A BIPOLAR ELECTROSURGICAL INSTRUMENT

CROSS REFERENCE TO RELATED APPLICATION

The present application claims the benefit of and priority to U.S. Provisional Application Ser. No. 61/881,529, filed on Sep. 24, 2013, the entire contents of which are incorporated herein by reference.

BACKGROUND

1. Technical Field

The present disclosure relates to electrosurgical instruments. More particularly, the present disclosure relates to a bipolar electrosurgical instrument, such as, for example, a vessel-sealing device, including a jaw assembly that includes an electrode adapted for tissue dissection and coagulation.

2. Discussion of Related Art

Electrosurgical instruments have become widely used by surgeons. Electrosurgery involves the application of electrical energy and/or electromagnetic energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery can be performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue. In monopolar electrosurgery, a patient return electrode, also called a grounding pad, bovie pad, neutral electrode or patient plate, is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode. In bipolar electrosurgery, both the active electrode and return electrode functions are performed at the site of surgery. Bipolar electrosurgical devices include two electrodes of opposite polarity that are located in proximity to one another for the application of current between their surfaces. Bipolar electrosurgical current travels from one electrode, through the intervening tissue to the other electrode to complete the electrical circuit, thereby eliminating the need for a remotely-located current return. Bipolar instruments generally include end-effectors, such as grippers, cutters, forceps, dissectors and the like.

Forceps utilize mechanical action to constrict, grasp, dissect and/or clamp tissue. By utilizing an electrosurgical forceps, a surgeon can utilize both mechanical clamping action and electrosurgical energy to effect hemostasis by heating the tissue and blood vessels to cauterize, coagulate/desiccate, seal and/or divide tissue. Bipolar electrosurgical forceps utilize two generally opposing electrodes that are operably associated with the inner opposing surfaces of an end effector and that are both electrically coupled to an electrosurgical generator. In bipolar forceps, the end-effector assembly generally includes opposing jaw assemblies pivotably mounted with respect to one another. In bipolar configuration, only the tissue grasped between the jaw assemblies is included in the electrical circuit.

By utilizing an electrosurgical forceps, a surgeon can cauterize, coagulate/desiccate and/or seal tissue and/or simply reduce or slow bleeding by controlling the intensity, frequency and duration of the electrosurgical energy applied through the jaw assemblies to the tissue. During the sealing process, mechanical factors such as the pressure applied between opposing jaw assemblies and the gap distance between the electrically-conductive tissue-contacting surfaces (electrodes) of the jaw assemblies play a role in determining the resulting thickness of the sealed tissue and effectiveness of the seal.

A variety of types of end-effector assemblies have been employed for various types of electrosurgery using a variety of types of monopolar and bipolar electrosurgical instruments.

SUMMARY

A continuing need exists for jaw assembly components that can be readily integrated into manufacturing assembly processes for the production of end-effector assemblies for use in electrosurgical instruments, such as electrosurgical forceps.

According to an aspect of the present disclosure, an end-effector assembly is provided. The end-effector assembly includes opposing first and second jaw assemblies, at least one of the first and second assemblies is movable relative to the other from a first position wherein the jaw assemblies are disposed in spaced relation relative to one another to at least a second position closer to one another wherein the jaw assemblies cooperate to grasp tissue therebetween. The first jaw assembly includes a first housing and a first electrically-conductive tissue-engaging structure associated with at least a portion of the first housing. The second jaw assembly includes a second housing and a second electrically-conductive tissue-engaging structure associated with at least a portion of the second housing. The end-effector assembly also includes a dissector electrode coupled along at least a portion of a lateral side portion of either one of the first housing or the second housing. The dissector electrode is electrically-isolated from the first and second electrically-conductive tissue-engaging structures.

According to another aspect of the present disclosure, a bipolar forceps is provided. The bipolar forceps includes a housing having a shaft affixed thereto. The shaft includes opposing jaw assemblies attached to a distal end thereof. At least one of jaw assemblies is movable relative to the other from a first position wherein the jaw assemblies are disposed in spaced relation relative to one another to at least a second position closer to one another wherein the jaw assemblies cooperate to grasp tissue therebetween. Each jaw assembly includes an outer housing and an electrically-conductive tissue-engaging structure associated with at least a portion of the outer housing. The bipolar forceps also includes one or more dissector electrodes coupled along at least a portion of a lateral side portion of either one of housings. The one or more dissector electrodes are electrically-isolated from the electrically-conductive tissue-engaging structures. A current return path during activation of the at least one dissector electrode includes either one of the electrically-conductive tissue-engaging structures.

According to another aspect of the present disclosure, a bipolar forceps is provided that includes a housing having a shaft affixed thereto. The shaft includes first and second jaw assemblies attached to a distal end thereof. At least one of the first and second jaw assemblies is movable relative to the other from a first position wherein the jaw assemblies are disposed in spaced relation relative to one another to at least a second position closer to one another wherein the jaw assemblies cooperate to grasp tissue therebetween. The first jaw assembly includes a first outer housing and a first electrically-conductive tissue-engaging structure disposed in association with at least a portion of the first outer housing. The second jaw assembly includes a second outer housing and a second electrically-conductive tissue-engaging structure disposed in association with at least a portion of the second outer housing. The bipolar forceps also includes first and second dissector electrodes. The first dissector electrode is coupled along at least a portion of a first lateral side of the first outer housing, wherein the first dissector electrode is electrically-isolated from the first electrically-conductive tissue-engaging structure. The second dissector electrode is coupled along at least a portion of a second lateral side of the second outer housing, wherein the second dissector electrode is electrically-isolated from the second electrically-conductive tissue-engaging structure. The bipolar forceps is adapted to allow each one of the first and second dissector electrodes to be individually activated.

BRIEF DESCRIPTION OF THE DRAWINGS

Objects and features of the presently-disclosed jaw assemblies including an electrode adapted for tissue dissection and coagulation for use in electrosurgical instruments will become apparent to those of ordinary skill in the art when descriptions of various embodiments thereof are read with reference to the accompanying drawings, of which.

DETAILED DESCRIPTION

Hereinafter, embodiments of jaw assemblies for use in electrosurgical instruments of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide electrosurgical instruments suitable for sealing, cauterizing, coagulating/desiccating, cutting and/or dissecting vessels and vascular tissue. Various embodiments of the present disclosure provide an electrosurgical forceps with an end-effector assembly including two jaw assemblies disposed in opposing relation relative to one another. Various embodiments of the presently-disclosed jaw assemblies include one or more dissector electrodes adapted for tissue dissection and coagulation. Embodiments of the presently-disclosed end-effector assemblies may include jaw assemblies arranged in a unilateral or bilateral configuration.

Embodiments of the presently-disclosed electrosurgical forceps including a dissector electrode may be suitable for utilization in endoscopic surgical procedures and/or suitable for utilization in open surgical applications. Embodiments of the presently-disclosed electrosurgical instruments may be connected through a suitable bipolar cable to a generator and/or other suitable power source. Although the following description describes the use of an endoscopic bipolar forceps, the teachings of the present disclosure may also apply to a variety of electrosurgical devices that include jaw assemblies.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 1:
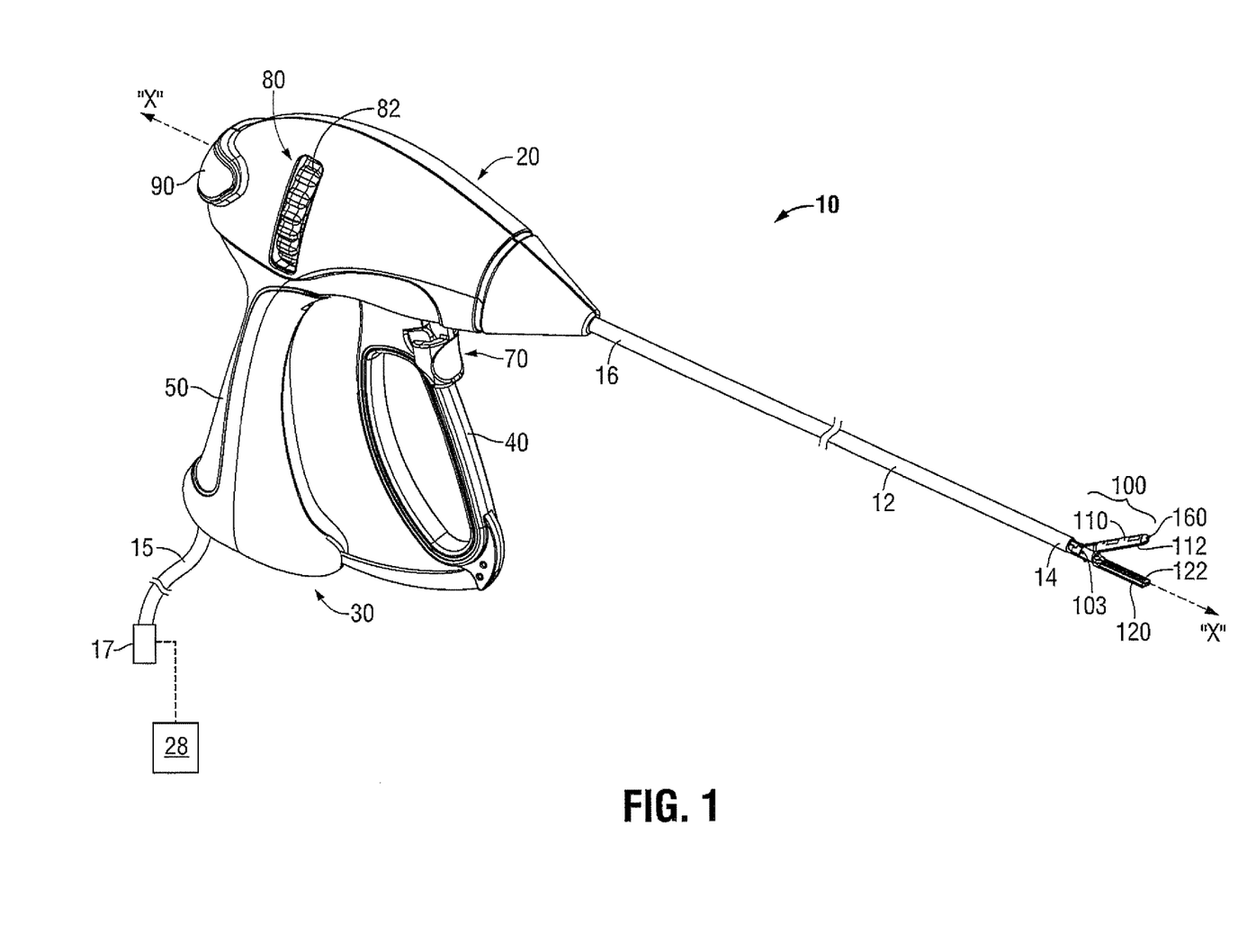
FIG. 1 is a right, side view of an endoscopic bipolar forceps showing a housing, a rotatable member, a shaft and an end-effector assembly in accordance with an embodiment of the present disclosure.

In FIG. 1, an embodiment of an endoscopic bipolar forceps 10 is shown for use with various surgical procedures and generally includes a housing 20, a handle assembly 30, a rotatable assembly 80, a trigger assembly 70, and an end-effector assembly 100. End-effector assembly 100 generally includes two jaw assemblies 110 and 120 disposed in opposing relation relative to one another. An embodiment of the end-effector assembly 100, in accordance with the present disclosure, is shown in more detail in FIG. 3. It is to be understood, however, that other end-effector embodiments may also be used. One or more components of the bipolar forceps 10, e.g., the housing 20, the handle assembly 30, the rotatable assembly 80, the trigger assembly 70, and/or the end-effector assembly 100, may be adapted to mutually cooperate to grasp, seal and/or divide tissue, e.g., tubular vessels and vascular tissue (not shown). Forceps 10 may include additional, fewer, or different components than shown in FIG. 1, depending upon a particular purpose or to achieve a desired result.

End-effector assembly 100 includes a dissector electrode 160 adapted for tissue dissection and coagulation. Dissector electrode 160, which is described in more detail later in this description, may include any suitable electrically-conductive material, including, without limitation, metals, metal alloys, electrically-conductive polymers, and composite materials. Dissector electrode 160 may be formed as a multi-layer configuration of materials. In some embodiments, one or more portions of the dissector electrode 160, e.g., an inner-facing surface(s) thereof, may include an non-electrically-conductive or substantially non-electrically-conductive material configured to provide for electrical isolation between electrically-conductive elements of the dissector electrode 160 (e.g., tip portion 169 and/or shoulder portion 168) and one or more jaw assembly components, e.g., to reduce the chances of short circuiting the jaw assemblies 110 and 120 during activation, and/or to facilitate assembly and/or to meet specific tolerance requirements for proper jaw alignment, thermal resistance, strength and rigidity, which play a role in determining the reliability and effectiveness of electrosurgical instruments.

In some embodiments, as shown in FIG. 1, the end-effector assembly 100 includes jaw assemblies 110 and 120 in a unilateral configuration and the dissector electrode 160 is disposed in association with the movable jaw assembly 110. In alternative embodiments, a dissector electrode adapted for tissue dissection and coagulation (e.g., dissector electrode 660 shown in FIGS. 6 and 7) may be disposed in association with the fixed jaw assembly (e.g., 620 shown in FIGS. 6 and 7). In alternative embodiments, wherein two jaw assemblies disposed in opposing relation relative to one another are arranged in a bilateral configuration, a dissector electrode in accordance with the present disclosure may be disposed in association either one of the bilateral jaw assemblies.

Although FIG. 1 depicts a bipolar forceps 10 for use in connection with endoscopic surgical procedures, the teachings of the present disclosure may also apply to more traditional open surgical procedures. For the purposes herein, the forceps 10 is described in terms of an endoscopic instrument; however, an open version of the forceps (e.g., bipolar forceps 200 shown in FIG. 2) may also include the same or similar operating components and features as described below.

Forceps 10 includes a shaft 12 having a distal end 14 configured to mechanically engage the end-effector assembly 100 and a proximal end 16 configured to mechanically engage the housing 20. In some embodiments, the shaft 12 has a length from the proximal side of the handle assembly 30 to the distal side of the forceps 10 in a range of about 7 centimeters to about 44 centimeters. End-effector assembly 100 may be selectively and releaseably engageable with the distal end 14 of the shaft 12, and/or the proximal end 16 of the shaft 12 may be selectively and releaseably engageable with the housing 20 and the handle assembly 30.

The proximal end 16 of the shaft 12 is received within the housing 20, and connections relating thereto are disclosed in commonly assigned U.S. Pat. No. 7,150,097 entitled "METHOD OF MANUFACTURING JAW ASSEMBLY FOR VESSEL SEALER AND DIVIDER," commonly assigned U.S. Pat. No. 7,156,846 entitled "VESSEL SEALER AND DIVIDER FOR USE WITH SMALL TROCARS AND CANNULAS," commonly assigned U.S. Pat. No. 7,597,693 entitled "VESSEL SEALER AND DIVIDER FOR USE WITH SMALL TROCARS AND CANNULAS" and commonly assigned U.S. Pat. No. 7,771,425 entitled "VESSEL SEALER AND DIVIDER HAVING A VARIABLE JAW CLAMPING MECHANISM."

In some embodiments, as shown in FIG. 1, forceps 10 includes an electrosurgical cable 15. Electrosurgical cable 15 may be formed from a suitable flexible, semi-rigid or rigid cable, and may connect directly to an electrosurgical power generating source 28. In some embodiments, the electrosurgical cable 15 connects the forceps 10 to a connector 17, which further operably connects the instrument 10 to the electrosurgical power generating source 28. Cable 15 may be internally divided into one or more cable leads each of which transmits energy through their respective feed paths to the end-effector assembly 100.

Electrosurgical power generating source 28 may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ™, FORCE FX™, and FORCE TRIAD™ sold by Covidien Surgical Solutions of Boulder, Colo. Forceps 10 may alternatively be configured as a battery-powered wireless instrument.

End-effector assembly 100 may be configured as a unilateral assembly, i.e., the end-effector assembly 100 may include a stationary or fixed jaw assembly, e.g., 120, mounted in fixed relation to the shaft 12, and a moveable jaw assembly, e.g., 110, mounted about a pivot pin 103 coupled to the fixed jaw assembly. Alternatively, the forceps 10 may include a bilateral assembly, i.e., both jaw assemblies 110 and 120 are moveable relative to one another. Jaw assemblies 110 and 120 may be curved at various angles to facilitate manipulation of tissue and/or to provide enhanced line-of-sight for accessing targeted tissues.

As shown in FIG. 1, the end-effector assembly 100 is rotatable about a longitudinal axis "X-X" through rotation, either manually or otherwise, of the rotatable assembly 80. Rotatable assembly 80 generally includes two halves (not shown), which, when assembled about a tube of shaft 12, form a generally circular rotatable member 82. Rotatable assembly 80, or portions thereof, may be configured to house a drive assembly (not shown) and/or a knife assembly (not shown), or components thereof. A reciprocating sleeve (not shown) is slidingly disposed within the shaft 12 and remotely operable by the drive assembly (not shown). Examples of rotatable assembly embodiments, drive assembly embodiments, and knife assembly embodiments of the forceps 10 are described in the above-mentioned, commonly-assigned U.S. Pat. Nos. 7,150,097, 7,156,846, 7,597,693 and 7,771,425.

Handle assembly 30 includes a fixed handle 50 and a movable handle 40. In some embodiments, the fixed handle 50 is integrally associated with the housing 20, and the movable handle 40 is selectively movable relative to the fixed handle 50. Movable handle 40 of the handle assembly 30 is ultimately connected to the drive assembly (not shown). As can be appreciated, applying force to move the movable handle 40 toward the fixed handle 50 pulls the drive sleeve (not shown) proximally to impart movement to the jaw assemblies 110 and 120 from an open position, wherein the jaw assemblies 110 and 120 are disposed in spaced relation relative to one another, to a clamping or closed position, wherein the jaw assemblies 110 and 120 cooperate to grasp tissue therebetween. Examples of handle assembly embodiments of the forceps 10 are described in the above-mentioned, commonly-assigned U.S. Pat. Nos. 7,150,097, 7,156,846, 7,597,693 and 7,771,425.

Forceps 10 includes a switch 90 configured to permit the user to selectively activate the forceps 10 in a variety of different orientations, i.e., multi-oriented activation. As can be appreciated, this simplifies activation. When the switch 90 is depressed, electrosurgical energy is transferred through one or more electrical leads (not shown) to the jaw assemblies 110 and 120. Although FIG. 1 depicts the switch 90 disposed at the proximal end of the housing assembly 20, switch 200 may be disposed on another part of the forceps 10 (e.g., the fixed handle 50, rotatable member 82, etc.) or another location on the housing assembly 20.

Figure 3:
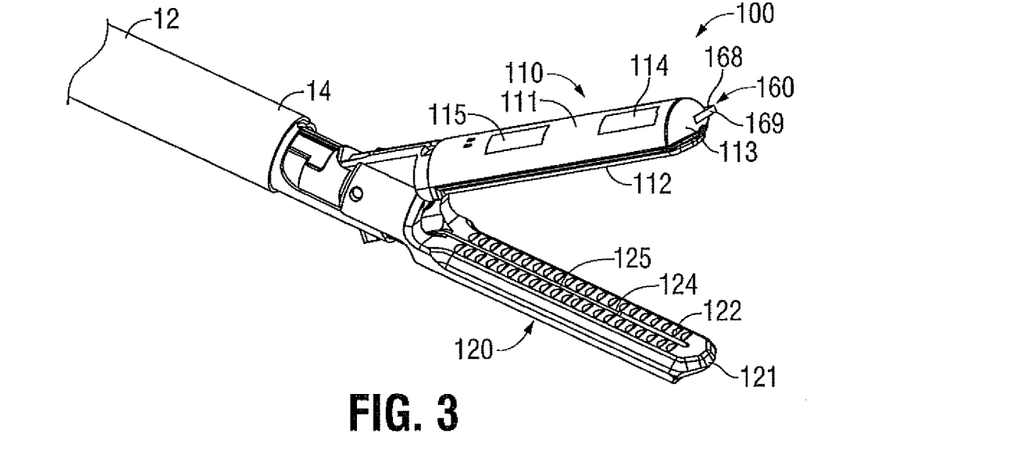
FIG. 3 is a perspective view of the jaw assembly of the end-effector assembly of the bipolar forceps of FIG. 1 shown with an electrode adapted for tissue dissection and coagulation in accordance with an embodiment of the present disclosure.

Jaw assemblies 110 and 120, as shown in FIGS. 1 and 3, include an electrically-conductive tissue-engaging surface or sealing plate 112 and 122, respectively, arranged in opposed relation relative to one another and disposed in association with an outer housing 111 and 121, respectively (FIG. 3). In some embodiments, the outer housings 111 and 121 define a cavity therein configured to at least partially encapsulate and/or securely engage the sealing plates 112 and 122, respectively, and/or other jaw assembly components.

In some embodiments, the outer housings 111 and 121 may be formed, at least in part, of an non-electrically-conductive or substantially non-electrically-conductive material. Outer housing 111 and/or the outer housing 121 include one or more electrically-conductive portions suitably disposed relative to the dissector electrode 160 to provide a current return path. In some embodiments, as shown in FIG. 3, the outer housing 111 includes two electrically-conductive portions 114 and 115 configured to provide a current return path. The shape, size, and relative location of the electrically-conductive portions 114 and 115, e.g., in relation to the dissector electrode 160, may be varied from the configuration depicted in FIG. 3. Additionally, or alternatively, the outer housing 121 may include one or more electrically-conductive portions suitably disposed to provide a current return path.

Dissector electrode 160 includes a tip portion 169 and a shoulder portion 168. In some embodiments, the tip portion 169 may extend distally beyond the distal end 113 of the outer housing 111. Tip portion 169 may be configured to provide a desired function, and may include curves at various angles to facilitate contact with targeted tissue. In some embodiments, the tip portion 169 is configured for dissection, and may include a sharp knife edge, a blunt tip, a blunt edge, paddle, hook, a ball-shaped portion, or another shape. Shoulder portion 168 extends along at least a portion of a lateral side portion of the outer housing 111. In some embodiments, the shoulder portion 168 is configured for coagulation. The shape and size of the shoulder portion 168 may be varied from the configuration depicted in FIGS. 1 and 3, e.g., depending upon a particular purpose.

Sealing plates 112 and 122 may be adapted to connect to an electrosurgical energy source (e.g., 28 shown in FIG. 1) independently of one another such that either or both of the sealing plates 112 and 122 may be selectively energized, depending on a particular purpose. In some embodiments, the jaw assembly 110 is connected to a first electrical lead (not shown) and the jaw assembly 120 is connected to a second electrical lead (not shown), which, in turn, are electrically coupled with an electrosurgical energy source (e.g., 28 shown in FIG. 1). In some embodiments, the first and second electrical leads terminate within the outer housings 111 and 121, respectively, e.g., electro-mechanically coupled to the sealing plates 112 and 122, respectively, and may allow a user to selectively supply either bipolar or monopolar electrosurgical energy to the jaw assemblies 110 and 120 as needed during surgery. Activation switch 90 (FIG. 1) is selectively actuatable to control the supply of energy to the sealing plates 112 and 122. Activation switch 90 may include one or more switch components to facilitate selective activation of either or both of the sealing plates 112 and 122.

One or both of the jaw assemblies 110 and 120 include a longitudinally-oriented slot or knife channel configured to permit reciprocation of a knife blade (not shown). In some embodiments, as shown in FIG. 3, the knife channel 125 may be completely disposed in one of the two jaw assemblies, e.g., jaw assembly 120, depending upon a particular purpose.

Examples of sealing plate 112, 122, outer housing 111, 121, and knife blade embodiments are disclosed in commonly assigned International Application Serial No. PCT/US01/11412 filed on Apr. 6, 2001, entitled "ELECTROSURGICAL INSTRUMENT WHICH REDUCES COLLATERAL DAMAGE TO ADJACENT TISSUE," and commonly assigned International Application Serial No. PCT/US01/11411 filed on Apr. 6, 2001, entitled "ELECTROSURGICAL INSTRUMENT REDUCING FLASHOVER."

Figure 2:
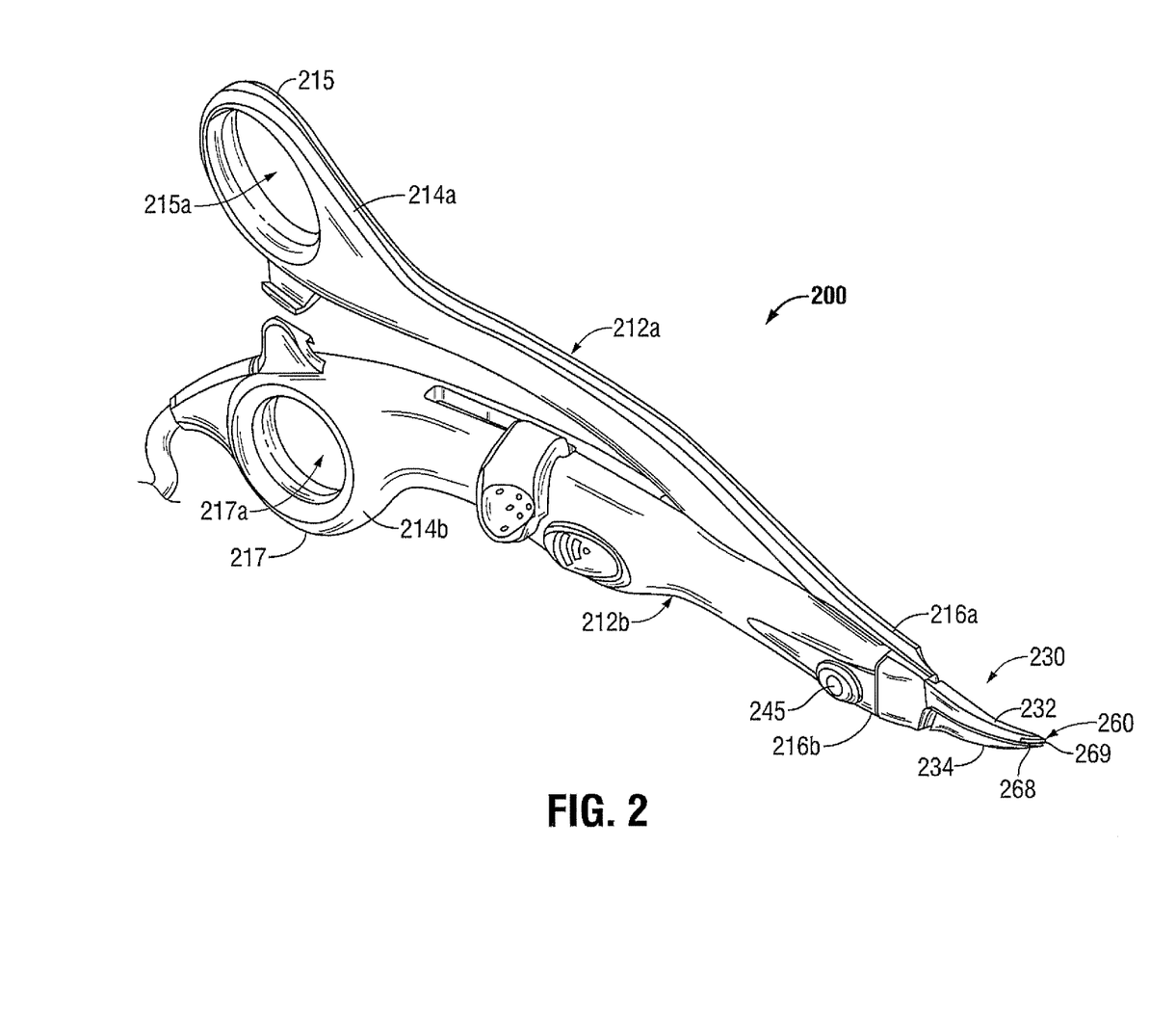
FIG. 2 is a perspective view of an open bipolar forceps according to an embodiment of the present disclosure.

In FIG. 2, an embodiment of an open forceps 200 is shown for use with various surgical procedures and generally includes an end effector assembly 230 operably associated with a pair of opposing shafts 212*a* and 212*b* and disposed in association with the distal ends 216*a* and 216*b* thereof, respectively. End effector assembly 230 includes a first jaw member 232 and a second jaw member 234 disposed in opposing relation relative to one another and pivotably connected about a pivot pin 245 and movable relative to one another to grasp tissue.

Shaft 212a includes a handle 215 disposed in association with the proximal end 214a thereof. Shaft 212b includes a handle 217 disposed in association with the proximal end 214b thereof. Handles 215 and 217 define a finger and/or thumb hole 215a and 217a, respectively, therethrough for receiving the user's finger or thumb. Finger and/or thumb holes 215a and 217a facilitate movement of the shafts 212a and 212b relative to one another to pivot the first and second jaw members 232 and 234 from an open position, wherein the first and second jaw members 232 and 234 are disposed in spaced relation relative to one another, to a clamping or closed position, wherein the first and second jaw members 232 and 234 cooperate to grasp tissue therebetween.

End-effector assembly 230 includes a dissector electrode 260 adapted for tissue dissection and coagulation. Dissector electrode 260 includes a shoulder portion 268. The shape and size of the shoulder portion 268 may be varied from the configuration depicted in FIG. 2, e.g., depending upon a particular purpose. Dissector electrode 260 may include a tip portion 269.

In some embodiments, as shown in FIG. 2, the dissector electrode 260 is disposed in association with the first jaw member 232. In alternative embodiments, the dissector electrode 260 may be disposed in association with the second jaw member 234. Dissector electrode 260 include any suitable electrically-conductive material, and may be formed as a multi-layer configuration of materials. In some embodiments, one or more portions of the dissector electrode 260 may include an non-electrically-conductive or substantially non-electrically-conductive material. Dissector electrode 260 shown in FIG. 2 is similar to the dissector electrode 160 shown in FIGS. 1 and 3, and further description of the like elements is omitted in the interests of brevity.

Figure 4:
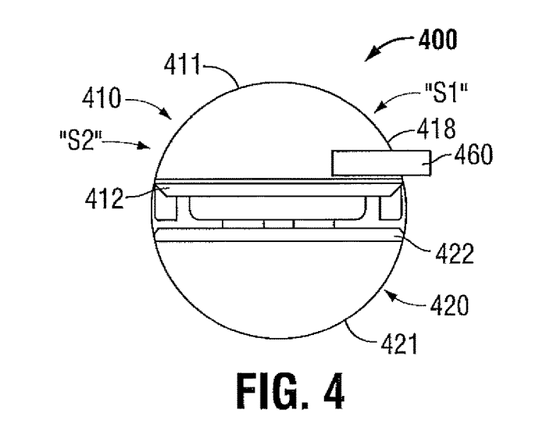
FIG. 4 is an enlarged, end view of another embodiment of a jaw assembly, similar to the jaw assembly of FIG. 3, shown with an electrode adapted for tissue dissection and coagulation in accordance with the present disclosure.
Figure 5:
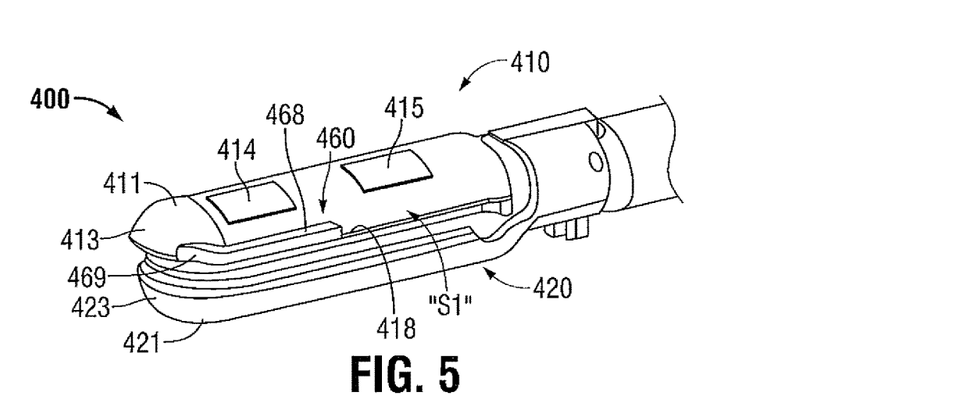
FIG. 5 is a left, side view of the jaw assembly shown in FIG. 4.

FIGS. 4 and 5 show an end-effector assembly 400 in accordance with an embodiment of the present disclosure that includes a dissector electrode 460 adapted for tissue dissection and coagulation. Dissector electrode 460 includes a tip portion 469 and a shoulder portion 468 as best shown in FIG. 5.

End-effector assembly 400 generally includes two jaw assemblies 410 and 420 disposed in opposing relation relative to one another. Jaw assemblies 410 and 420 each include an electrically-conductive tissue-engaging surface or sealing plate 412 and 422, respectively, arranged in opposed relation relative to one another and disposed in association with an outer housing 411 and 421, respectively.

Outer housings 411 and 421 generally include a distal end 413 and 423, respectively, and two lateral side portions (e.g., first lateral side portion "S1" and second lateral side portion "S2" of the housing 411 shown in FIG. 4). In some embodiments, the outer housings 411 and 421 may be formed, at least in part, of an non-electrically-conductive or substantially non-electrically-conductive material. Outer housing 411 and/or the outer housing 421 may include one or more electrically-conductive portions of suitable conductivity and so disposed in relation to one or more features of the dissector electrode 460 (e.g., tip portion 469 and/or shoulder portion 468) to provide a current return path. In some embodiments, as shown in FIG. 5, the outer housing 411 includes two electrically-conductive portions 414 and 415 configured to provide a current return path. The shape, size, and relative location of the electrically-conductive portions 414 and 415, e.g., in relation to the dissector electrode 460, may be varied from the configuration depicted in FIG. 5.

In some embodiments, the tip portion 469 of the dissector electrode 460 may extend distally beyond the distal end 413 of the outer housing 411. Tip portion 469 may be configured to provide a desired function, and may include curves at various angles to facilitate contact with targeted tissue. Tip portion 469 may include a sharp knife edge, a blunt tip, a blunt edge, paddle, hook, a ball-shaped portion, or another shape. Shoulder portion 468 extends along at least a portion of the first lateral side portion "S1" of the outer housing 411. Shoulder portion 468 may have any suitable dimensions, e.g., length, width and height. The shape and size of the shoulder portion 468 may be varied from the configuration depicted in FIG. 5. In some embodiments, the tip portion 469 is configured for dissection, and the shoulder portion 468 is configured for coagulation.

Dissector electrode 460 may include any suitable electrically-conductive material, including, without limitation, metals, metal alloys, electrically-conductive polymers, and composite materials. In some embodiments, one or more portions of the dissector electrode 460, e.g., an inner-facing surface(s) thereof, may include an non-electrically-conductive or substantially non-electrically-conductive material configured to provide for electrical isolation between electrically-conductive elements of the dissector electrode 460 (e.g., tip portion 469 and/or shoulder portion 468) and one or more jaw assembly components, e.g., to reduce the chances of short circuiting the jaw assemblies 410 and 420 during activation, and/or to facilitate assembly and/or to meet specific tolerance requirements for proper jaw alignment, thermal resistance, strength and rigidity, which play a role in determining the reliability and effectiveness of electrosurgical instruments.

In some embodiments, one or more portions of the dissector electrode 460, e.g., an inner-facing surface(s) thereof, may include an non-electrically-conductive or substantially non-electrically-conductive material suitably configured to provide for electrical isolation between electrically-conductive elements of the dissector electrode 460 (e.g., tip portion 469 and/or shoulder portion 468) and one or more jaw assembly components, e.g., to facilitate assembly and/or to meet specific tolerance requirements for proper jaw alignment, thermal resistance, strength and rigidity.

Figure 6:
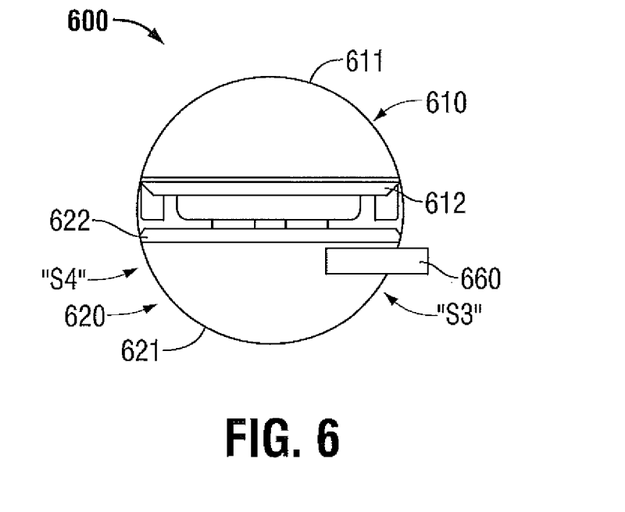
FIG. 6 is an enlarged, end view of still another embodiment of a jaw assembly including an electrode adapted for tissue dissection and coagulation in accordance with the present disclosure.
Figure 7:
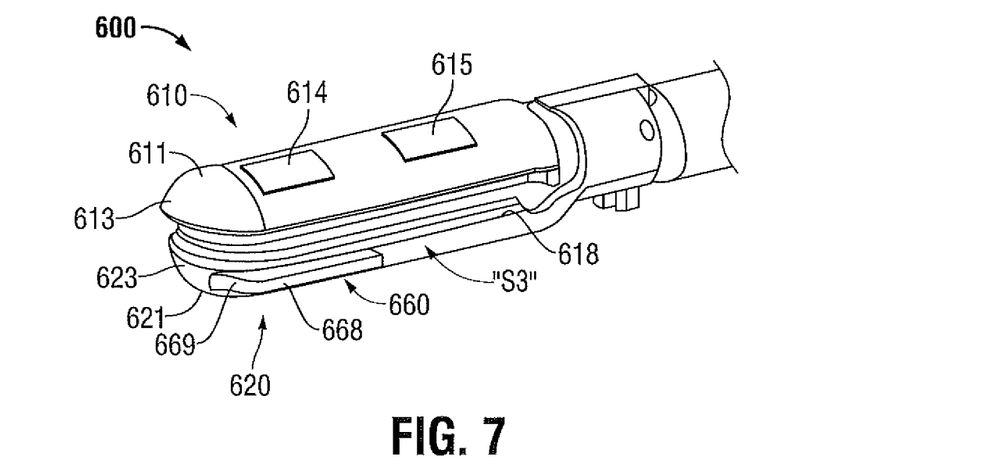
FIG. 7 is a left, side view of the jaw assembly shown in FIG. 6.

FIGS. 6 and 7 show an end-effector assembly 600 in accordance with an embodiment of the present disclosure that includes a dissector electrode 660 adapted for tissue dissection and coagulation. End-effector assembly 600 generally includes two jaw assemblies 610 and 620 disposed in opposing relation relative to one another. Jaw assemblies 610 and 620 each include an tissue-engaging surface or sealing plate 612 and 622, respectively, disposed in association with an outer housing 611 and 621, respectively, and arranged in opposed relation relative to one another. Dissector electrode 660 is generally insulated from the sealing plates 612 and 622. Dissector electrode 660 may be insulated, at least in part, from one or more electrically-conductive portions of the outer housing 611 and/or the outer housing 621.

Outer housings 611 and 621 include distal ends 613 and 623, respectively, and are configured to define two lateral side portions (e.g., first lateral side portion "S1" and second lateral side portion "S3" extending distally from the distal end 613 of the housing 621 as shown in FIG. 6). Outer housings 611 and 621 may be formed, at least in part, of an electrically-insulative material. In some embodiments, the outer housing 611 and/or the outer housing 621 include a configuration of one or more electrically-conductive portions suitably disposed relative to the dissector electrode 660 to provide a current return path. In some embodiments, as shown in FIG. 7, the outer housing 611 includes two electrically-conductive portions 614 and 615 configured to provide a current return path. The shape, size, and relative location of the electrically-conductive portions 614 and 615, e.g., in relation to the dissector electrode 660, may be varied from the configuration depicted in FIG. 7.

Dissector electrode 660 may include any suitable electrically-conductive material, including, without limitation, metals, metal alloys, polymers, and composite materials. Dissector electrode 660 may be formed as a multi-layer configuration of materials. In some embodiments, one or more portions of the dissector electrode 660, e.g., an inner-facing surface(s) thereof, may include an non-electrically-conductive or substantially non-electrically-conductive material suitably configured to provide for electrical isolation between electrically-conductive elements of the dissector electrode 660 (e.g., tip portion 669 and/or shoulder portion 668) and a configuration of one or more electrically-conductive portions of the jaw assemblies 610 and 620, e.g., to facilitate assembly, and/or to ensure electrical isolation either in connection with, or independently from, the configuration of electrically-insulative bushings used to electrically isolate the opposing jaw assemblies 610 and 620 from one another.

In alternative embodiments, a dissector electrode, and/or components thereof, e.g., a shoulder portion, may be disposed in association with the second lateral side portion "S4" of the outer housing 621. In some embodiments, the end-effector assembly 600 may be configured with two dissector electrodes, e.g., disposed in association with each of the first and second lateral side portions "S3" and "S4", respectively, e.g., to allow the user flexibility in the use of the end-effector assembly 600 to facilitate tissue dissection and coagulation.

Figure 8:
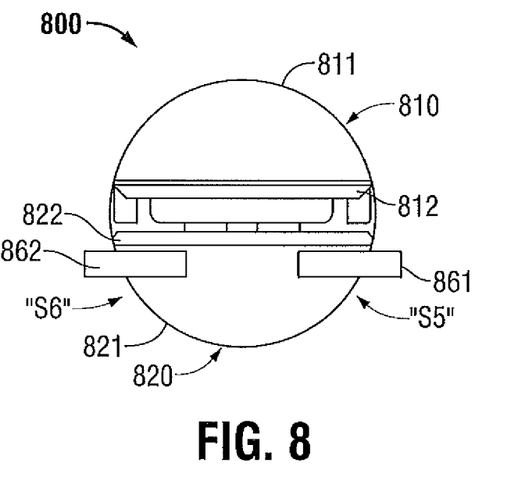
FIG. 8 is an enlarged, end view of a jaw assembly including two electrodes adapted for tissue dissection and coagulation in accordance with an embodiment of the present disclosure.

FIG. 8 shows an end-effector assembly 800 in accordance with an embodiment of the present disclosure that includes a first dissector electrode 861 and a second dissector electrode 862, e.g., adapted for tissue dissection and coagulation. End-effector assembly 800 generally includes two jaw assemblies 810 and 820 disposed in opposing relation relative to one another. Jaw assemblies 810 and 820 each include an electrically-conductive tissue-engaging surface or sealing plate 812 and 822, respectively, arranged in opposed relation relative to one another and disposed in association with an outer housing 811 and 821, respectively. Jaw assemblies 810 and 820 shown in FIG. 8 are similar to the jaw assemblies 610 and 620, respectively, shown in FIGS. 6 and 7, and further description thereof is omitted in the interests of brevity.

First dissector electrode 861 is coupled along at least a portion of a lateral side portion "S5" of the outer housing 821 and the second dissector electrode 862 is coupled along at least a portion of a lateral side portion "S6" of the outer housing 821, such that the first and second dissector electrode 861 and 862, respectively, are disposed on the opposite sides of the jaw assembly 820. The first and second dissector electrodes 861 and 862, respectively, are similar to the dissector electrode 660 shown in FIGS. 6 and 7 and further description thereof is omitted in the interests of brevity.

Figure 9:
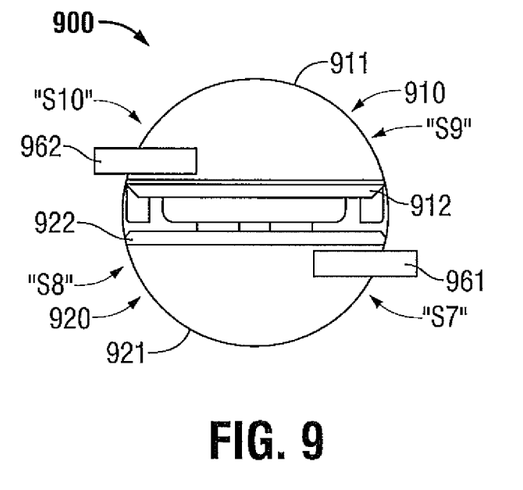
FIG. 9 is an enlarged, end view of another embodiment of a jaw assembly including two electrodes adapted for tissue dissection and coagulation in accordance with the present disclosure.

FIG. 9 shows an end-effector assembly 900 in accordance with an embodiment of the present disclosure that includes a first dissector electrode 961 and a second dissector electrode 962, e.g., adapted for tissue dissection and coagulation. End-effector assembly 900 generally includes two jaw assemblies 910 and 920 disposed in opposing relation relative to one another. Jaw assemblies 910 and 920 each include an electrically-conductive tissue-engaging surface or sealing plate 912 and 922, respectively, arranged in opposed relation relative to one another and disposed in association with an outer housing 911 and 921, respectively. Outer housing 921 includes a lateral side portion "S7" and a lateral side portion "S8", and the outer housing 911 includes a lateral side portion "S9" and a lateral side portion "S10".

In some embodiments, as show in FIG. 9, the first dissector electrode 961 is coupled along at least a portion of the lateral side portion "S7" of the outer housing 921, and the second dissector electrode 962 is coupled along at least a portion of the lateral side portion "S10" of the outer housing 811, such that the first and second dissector electrode 961 and 962, respectively, are disposed on the opposite sides of the jaw assemblies 920 and 910, respectively. The first and second dissector electrodes 961 and 962, respectively, are similar to the dissector electrode 660 shown in FIGS. 6 and 7 and further description thereof is omitted in the interests of brevity. In any of the above-described embodiments, an end-effector assembly having a plurality of dissector electrodes may be adapted to allow the dissector electrodes to be individually activated, e.g., depending upon a particular purpose.

In alternative embodiments compatible with any of the above embodiments of dissector electrodes for assembly into jaw assembly configurations, an electrically-insulative bushing may be used to electrically isolate the opposing jaw members from one another, wherein a configuration of one or more electrically-insulative bushings may be associated with either or both jaw assemblies.

In some embodiments, a configuration of one or more electrically-insulative bushings may additionally, or alternatively, be associated with one or more dissector electrodes. In some embodiments, the electrically-insulative bushing may include ceramic or any of a variety of suitable non-electrically conductive materials such as polymeric materials, e.g., plastics, and/or other insulative materials. In other embodiments, other non-electrically conductive synthetic and/or natural materials having suitable weight, strength, cost and/or other characteristics may be used for the electrically-insulative bushing(s).

The above-described bipolar forceps embodiments that include a dissector electrode adapted for tissue dissection and coagulation are capable of directing energy into tissue, and may be suitable for use in a variety of procedures and operations. The above-described end-effector embodiments may utilize both mechanical clamping action and electrical energy to effect hemostasis by heating tissue and blood vessels to coagulate, cauterize, cut and/or seal tissue. The jaw assemblies may be either unilateral or bilateral. The above-described bipolar forceps embodiments that include a dissector electrode adapted for tissue dissection and coagulation may be suitable for utilization with endoscopic surgical procedures and/or hand-assisted, endoscopic and laparoscopic surgical procedures. The above-described bipolar forceps embodiments that include a dissector electrode adapted for tissue dissection and coagulation may be suitable for utilization in open surgical applications.

The above-described end-effector embodiments may be used in connection with sealing plates and support bases of jaw assemblies of varied geometries, e.g., lengths and curvatures, such that variously-configured jaw assemblies may be fabricated and assembled into various end-effector configurations that include a dissector electrode adapted for tissue dissection and coagulation, e.g., depending upon design of specialized electrosurgical instruments.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An end-effector assembly, comprising:
    opposing first and second jaw assemblies, at least one of the first and second assemblies is movable relative to the other from a first position wherein the jaw assemblies are disposed in spaced relation relative to one another to at least a second position closer to one another wherein the jaw assemblies cooperate to grasp tissue therebetween;
    the first jaw assembly including:
        a first housing; and
        a first electrically-conductive tissue-engaging structure associated with at least a portion of the first housing;
    the second jaw assembly including a second housing, at least one of the first or second housings of the first and second jaw assemblies having an electrically-conductive outer surface configured to be coupled to an electrosurgical power generating source; and
    a dissector electrode protruding laterally from at least a portion of a lateral side portion of either one of the first housing or the second housing, wherein the dissector electrode is electrically-isolated from the first electrically-conductive tissue-engaging structure and the electrically-conductive outer surface.

2. The end-effector assembly of claim 1, wherein the electrically-conductive outer surface is configured to provide a current return path for electrosurgical energy emitted from at least one of the dissector electrode or the first electrically-conductive tissue-engaging structure.

3. The end-effector assembly of claim 1, wherein the jaw assemblies include one stationary jaw assembly and one movable jaw assembly mounted about a pivot pin coupled to the stationary jaw assembly.

4. The end-effector assembly of claim 1, wherein the dissector electrode is adapted for tissue dissection and coagulation.

5. The end-effector assembly of claim 1, wherein the dissector electrode further includes a shoulder portion protruding laterally from the lateral side portion of either one of the first housing or the second housing, the shoulder portion configured for coagulation.

6. The end-effector assembly of claim 5, wherein the dissector electrode further includes a tip portion protruding distally from a distal end of either one of the first housing or the second housing, the tip portion being sharper than the shoulder portion such that the tip portion is configured for dissection.

7. The bipolar forceps of claim 1, wherein the dissector electrode is laterally offset from a plane that intersects the first and second outer housings and that extends along a longitudinal axis defined by the first and second jaw assemblies.

8. A bipolar forceps, comprising:
    a housing having a shaft affixed thereto, the shaft including opposing jaw assemblies attached to a distal end thereof, at least one of which is movable relative to the other from a first position wherein the jaw assemblies are disposed in spaced relation relative to one another to at least a second position closer to one another wherein the jaw assemblies cooperate to grasp tissue therebetween, a first jaw assembly of the opposing jaw assemblies including an outer housing and an electrically-conductive tissue-engaging structure associated with at least a portion of the outer housing, a second jaw assembly of the opposing jaw assemblies including an outer housing, wherein the outer housing of at least one of the opposing jaw assemblies includes an electrically-conductive outer surface configured to be coupled to an electrosurgical power generating source; and
    at least one dissector electrode protruding laterally from at least a portion of a lateral side portion of either one of the outer housings, wherein the at least one dissector electrode is electrically-isolated from the electrically-conductive tissue-engaging structure and the electrically-conductive outer surface, wherein a current return path during activation of the at least one dissector electrode extends from the at least one dissector electrode to the electrically-conductive outer surface.

9. The bipolar forceps of claim 8, wherein the electrosurgical power generating source is connected to each jaw assembly such that the jaw assemblies are capable of conducting bipolar energy through tissue held therebetween to effect a tissue seal.

10. The bipolar forceps of claim 8, wherein the electrically-conductive outer surface is configured to provide a current return path for electrosurgical energy emitted from at least one of the electrically-conductive tissue-engaging structure or the at least one dissector electrode.

11. The bipolar forceps of claim 8, wherein the bipolar forceps is adapted to allow the at least one dissector electrode to be individually activated.

12. The bipolar forceps of claim 8, wherein the at least one dissector electrode is laterally offset from a plane that intersects the opposing jaw assemblies and that extends along a longitudinal axis defined by the opposing jaw assemblies.

13. A bipolar forceps, comprising:
    a housing having a shaft affixed thereto, the shaft including first and second jaw assemblies attached to a distal end thereof, at least one of the first and second assemblies is movable relative to the other from a first position wherein the jaw assemblies are disposed in spaced relation relative to one another to at least a second position closer to one another wherein the jaw assemblies cooperate to grasp tissue therebetween;
    the first jaw assembly including:
        a first outer housing; and
        a first electrically-conductive tissue-engaging structure disposed in association with at least a portion of the first outer housing;
    the second jaw assembly including a second outer housing, at least one of the first or second housings of the first and second jaw assemblies having an electrically-conductive outer surface configured to be coupled to an electrosurgical power generating source; and
    a first dissector electrode protruding laterally from at least a portion of a first lateral side of the first outer housing, wherein the first dissector electrode is electrically-isolated from the first electrically-conductive tissue-engaging structure and the electrically-conductive outer surface; and
    a second dissector electrode protruding laterally from at least a portion of a second lateral side of the second outer housing, wherein the second dissector electrode is electrically-isolated from the first electrically-conductive tissue-engaging structure and the electrically-conductive outer surface;

wherein the bipolar forceps is adapted to allow each one of the first and second dissector electrodes to be individually activated.

14. The bipolar forceps of claim 13, wherein the electrically-conductive outer surface is configured to provide a current return path for electrosurgical energy emitted from at least one of:

the first electrically-conductive tissue-engaging structure; or at least one of the first or second dissector electrodes.

15. The bipolar forceps of claim 13, wherein the first lateral side of the first outer housing and the second lateral side of the second outer housing are disposed on opposite sides of the first and second jaw assemblies.

16. The bipolar forceps of claim 13, wherein the first dissector electrode is laterally offset from a plane that intersects the first and second outer housings and that extends along a longitudinal axis defined by the shaft.

17. The bipolar forceps of claim 16, wherein the first dissector electrode is disposed on a first side of the plane, and the second dissector electrode is disposed on a second side of the plane.

18. The bipolar forceps of claim 17, wherein the first and second dissector electrodes are laterally spaced from one another.

* * * * *